(12) United States Patent  
McCarthy

(10) Patent No.: US 8,236,051 B2
(45) Date of Patent: Aug. 7, 2012

(54) APPARATUS FOR PLACEMENT IN THE ANNULUS OF A TRICUSPID VALVE

(75) Inventor: Patrick M. McCarthy, Chicago, IL (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1105 days.

(21) Appl. No.: 11/473,874

(22) Filed: Jun. 23, 2006

(65) Prior Publication Data
US 2007/0005134 A1 Jan. 4, 2007

Related U.S. Application Data

(60) Provisional application No. 60/694,441, filed on Jun. 27, 2005.

(51) Int. Cl.
*A61F 2/24* (2006.01)
(52) U.S. Cl. ........................ 623/2.38; 623/2.16
(58) Field of Classification Search .............. 623/2.38, 623/900, 904, 910, 2.36, 2.37, 2.12–2.19, 623/2.39–2.42
See application file for complete search history.

(56) References Cited

U.S. PATENT DOCUMENTS

| 3,744,060 | A | | 7/1973 | Bellhouse et al. |
| 4,576,605 | A | * | 3/1986 | Kaidash et al. ............. 623/2.39 |
| 4,816,029 | A | | 3/1989 | Penny, III et al. |
| 5,306,296 | A | | 4/1994 | Wright et al. |
| 5,607,471 | A | | 3/1997 | Seguin et al. |
| 5,776,189 | A | | 7/1998 | Khalid |
| 6,010,531 | A | * | 1/2000 | Donlon et al. ................. 623/2.1 |
| 6,749,630 | B2 | | 6/2004 | McCarthy et al. |
| 6,805,710 | B2 | | 10/2004 | Bolling et al. |
| 2003/0014105 | A1 | | 1/2003 | Cao |
| 2004/0006384 | A1 | | 1/2004 | McCarthy |
| 2005/0149181 | A1 | * | 7/2005 | Eberhardt .................... 623/2.14 |

FOREIGN PATENT DOCUMENTS

| EP | 0 595 791 A2 | | 5/1994 |
| WO | WO 95/28899 A1 | | 11/1995 |
| WO | WO 9700651 A1 | * | 1/1997 |
| WO | WO 00/74603 A1 | | 12/2000 |

* cited by examiner

*Primary Examiner* — Brian E. Pellegrino
(74) *Attorney, Agent, or Firm* — Tarolli, Sundheim, Covell & Tummino LLP

(57) ABSTRACT

An apparatus for implantation in an annulus of a tricuspid valve. The apparatus has an anterior annulus aspect, a posterior annulus aspect, and an atrioventricular (AV) node located adjacent the anterior annulus aspect. The apparatus includes an ovoid main body portion. The main body portion has an anterior body segment adapted for placement adjacent the anterior annulus aspect, a posterior body segment located opposite the anterior body portion and adapted for placement adjacent the posterior annulus aspect, and oppositely disposed left and right side body segments extending between the anterior and posterior body segments. At least two valve leaflets are secured within the main body portion and are coaptable to permit unidirectional flow of blood. A cushioned section is attached to the main body portion, coextends with a portion of the main body portion, and is adapted for placement adjacent the AV node.

7 Claims, 3 Drawing Sheets

APPARATUS FOR PLACEMENT IN THE ANNULUS OF A TRICUSPID VALVE

RELATED PATENT APPLICATION

This application claims priority to the filing date of U.S. Provisional Application No. 60/694,441, filed Jun. 27, 2005.

TECHNICAL FIELD

The present invention is directed to an apparatus for implantation in the annulus of a tricuspid valve.

BACKGROUND OF THE INVENTION

The human heart is a hollow muscular organ having four pumping chambers for pumping blood; namely, the left and right atria, and the left and right ventricles. The heart further includes four one-way valves located at either the entrance or the exit of the four chambers. The heart valves are identified as the aortic, mitral (or bicuspid), tricuspid and pulmonary valves. Each of these valves is mounted in an annulus comprising dense fibrous rings attached either directly or indirectly to the atrial and ventricular muscle fibers.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques may be used to repair a diseased or damaged valve. In a valve replacement operation, the damaged leaflets are excised and the annulus is sculpted to receive a replacement valve. Another less drastic method for treating defective valves is through repair or reconstruction, which is typically used on minimally calcified valves.

Effective placement of a replacement valve in the tricuspid position is difficult due to the anatomical structure of the tricuspid valve. The tricuspid valve includes an annulus and three leaflets extending inward into the flow orifice defined by the annulus. Chordae tendineae connect the leaflets to papillary muscles located in the right ventricle to control the movement of the leaflets.

Located in the lower interatrial septum is the atrioventricular (AV) node, which is a section of nodal tissue that delays cardiac impulses from the sinoatrial node to allow the atria to contract and empty their contents first, and also relays cardiac impulses to the AV bundle. Because of the location of the AV node, cardiac surgeons must avoid placing sutures too close to or within the AV node when implanting replacement valves in the tricuspid position. Excessive pressure on the AV node can disrupt the normal function of the AV node.

SUMMARY OF THE INVENTION

According to one embodiment of the present invention, an apparatus for implantation in the annulus of a tricuspid valve is described. The annulus has an anterior annulus aspect, a posterior annulus aspect, and an atrioventricular (AV) node located adjacent the anterior annulus aspect. The apparatus includes an ovoid main body portion. The main body portion has an anterior body segment adapted for placement adjacent the anterior annulus aspect, a posterior body segment located opposite the anterior body portion and adapted for placement adjacent the posterior annulus aspect, and oppositely disposed left and right side body segments extending between the anterior and posterior body segments. At least two valve leaflets are secured within the main body portion and are coaptable to permit unidirectional flow of blood. A cushioned section is attached to the main body portion, coextends at with at least a portion of the main body portion, and is adapted for placement adjacent the AV node.

The present invention further provides a method for implanting an apparatus in the annulus of a tricuspid valve having an anterior annulus aspect, a posterior annulus aspect, and an atrioventricular (AV) node located adjacent the anterior annulus aspect. According to the inventive method, an apparatus is provided. The apparatus has an ovoid main body portion, at least two valve leaflets secured within the main body portion and coaptable to permit unidirectional flow of blood, and a cushioned section attached to the main body portion and coextending at with at least a portion of the main body portion. The main body portion has an anterior body segment, a posterior body segment located opposite the anterior body portion, and oppositely disposed left and right side body segments extending between the anterior and posterior body segments. The apparatus is placed within the annulus of the tricuspid valve. The anterior body segment is positioned adjacent the anterior annulus aspect. The posterior body segment is positioned adjacent the posterior annulus aspect. The cushioned section is positioned adjacent the AV node. The apparatus is secured, as positioned, within the annulus of the tricuspid valve.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF EMBODIMENTS

Figure 1:
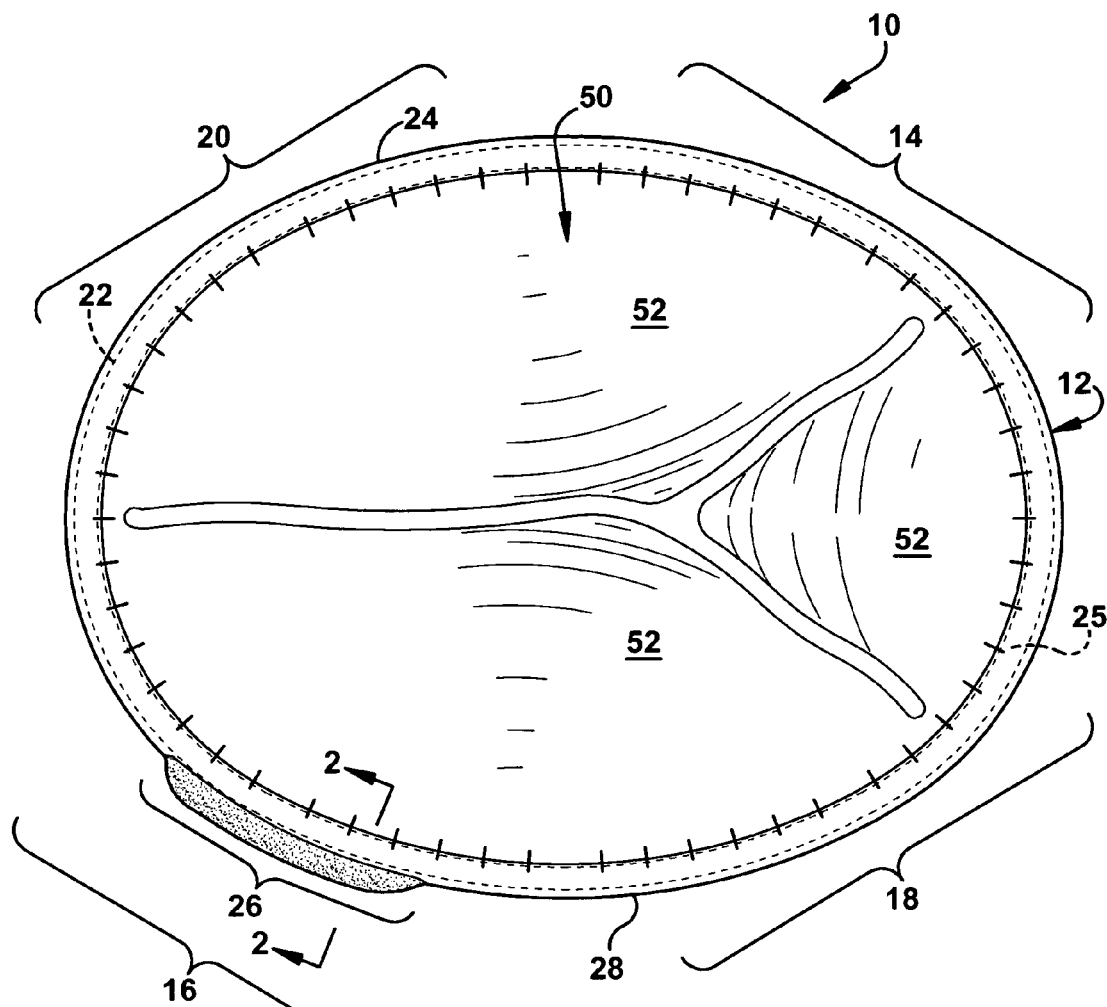
FIG. 1 is a plan view of an apparatus constructed in accordance with the present invention.

The present invention relates generally to atrioventricular (AV) valves, and more particularly to an apparatus for implantation in the annulus of a tricuspid valve. As representative of the present invention, FIG. 1 illustrates a three-dimensional (3D) apparatus 10 for implantation within an annulus 46 (FIG. 4) of a tricuspid valve 48 having three leaflets. The annulus 46 of the tricuspid valve 48 has an anterior aspect 44, a posterior aspect 42, and an AV node 40 located adjacent the anterior aspect of the tricuspid valve annulus.

As illustrated in FIG. 1, the apparatus 10 comprises a generally oval-shaped main body portion 12 having an anterior portion 16 adapted for placement against the anterior aspect 44 of the tricuspid valve annulus 46. The apparatus 10 further comprises a posterior portion 14, opposite the anterior portion 16, adapted for placement against the posterior aspect 42 of the tricuspid valve annulus 46. The apparatus 10 also includes oppositely disposed right and left side portions 18 and 20 extending between the anterior and posterior portions 16 and 14. Secured within the main body portion 12 is a bioprosthetic valve 50 having at least two valve leaflets 52 that are coaptable to permit unidirectional flow of blood. The main body portion 12 of the apparatus 10 has a 3D shape that conforms to the 3D shape of the tricuspid valve annulus 46.

The main body portion 12 of the apparatus 10 includes inner and outer layers 22 and 24. The inner layer 22 comprises an expandable support member 25. The structure of the support member 25 may be a mesh, a zigzag wire, a spiral wire, an expandable stent, or other suitable configuration. The support member 25 can be comprised of a material having a high modulus of elasticity, including, for example, cobalt-nickel alloys (e.g., Elgiloy), titanium, nickel-titanium alloys (e.g., Nitinol), cobalt-chromium alloys (e.g., Stellite), nickel-cobalt-chromium-molybdenum alloys (e.g., MP35N), graphite, ceramic, stainless steel, and hardened plastics.

The main body portion 12 of the apparatus 10 further includes the bioprosthetic valve 50 secured therein. The bioprosthetic valve 50 has at least two valve leaflets 52 that are coaptable to permit unidirectional flow of blood. The bioprosthetic valve 50 is secured by sutures or other suitable means within the main body portion 12 of the apparatus 10. In the illustrated embodiment, the bioprosthetic valve 50 is made from one or more pieces of biocompatible material formed into a tri-leaflet conduit having dimensions that correspond to the dimensions of the native tricuspid valve 48. The biocompatible material of the bioprosthetic valve 50 may be a harvested biological material including, but not limited to, bovine pericardial tissue, horse pericardial tissue, or porcine pericardial tissue. The biocompatible material may also be a suitable synthetic material including, but not limited to, polyurethane or expanded PTFE.

The outer layer 24 comprises a biocompatible covering 28 that encloses the support member 25. The biocompatible covering 28 may be comprised of silicone, polyerapthalate fabric, Dacron, polytetrafluoroethylene (PTFE) knit, expanded PTFE knit, polyester knit, or other biocompatible material. Sutures, clips, pins, staples, or other anchoring features may extend through the biocompatible covering 28 for anchoring the apparatus 10 in the valve annulus 46.

Figure 2:
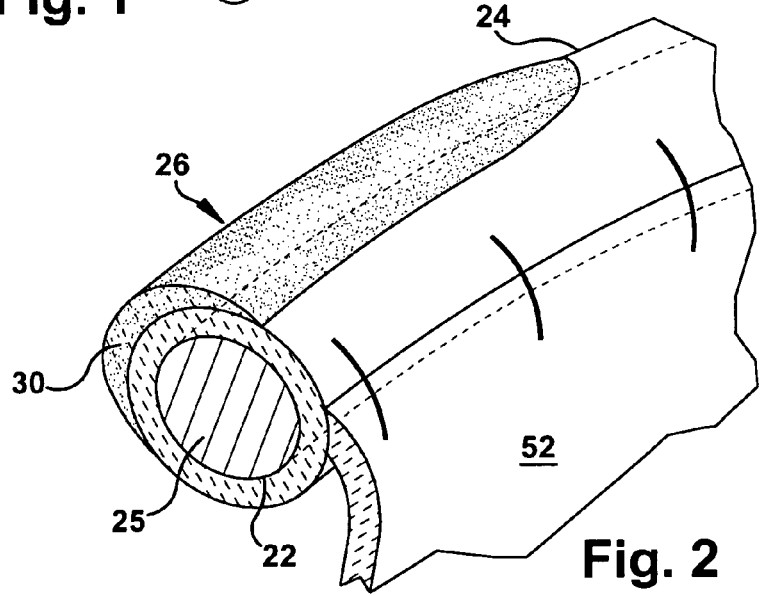
FIG. 2 is a cross-sectional view of the apparatus.
Figure 3:
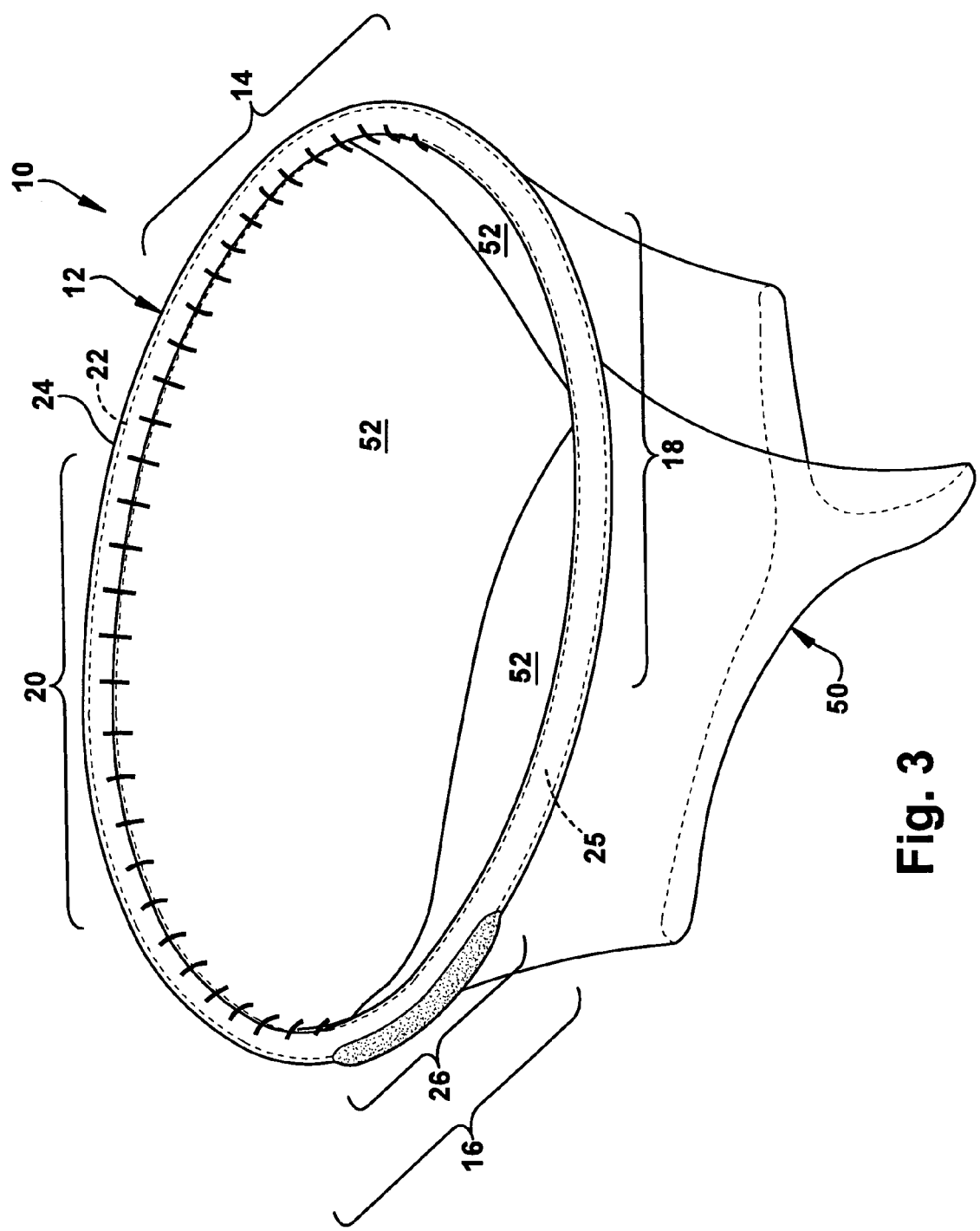
FIG. 3 is a perspective view of the apparatus.

FIG. 2 shows a cross-sectional view of the apparatus 10 through section 2-2 (FIG. 1). The outer layer 24 of the apparatus 10 includes a cushioned section 26 having an increased thickness formed by cushioning means 30. The cushioning means 30 is comprised of at least one material having generally flexible and resiliently yieldable properties. The cushioning means 30 may be made from the same or different materials as the biocompatible covering 28. Examples of materials which may comprise the cushioning means 30 include felt, velour, and biocompatible polymers such as PTFE-containing materials (e.g., GORE-TEX®). It is contemplated that the increased thickness formed by the cushioning means 30 could extend around the entire ring 10 to help further reduce perivalvular leaks.

The present invention further provides a method for implanting the apparatus 10 in the tricuspid valve annulus 46. Implantation of the apparatus 10 can be accomplished in a variety of ways. For instance, the apparatus 10 may be placed by percutaneous, surgical cut-down, or other minimally invasive techniques. By percutaneous techniques, it is meant that a location of the vasculature remote from the heart is accessed through the skin, such as using needle access through the Seldinger approach. Alternatively, the apparatus 10 could be implanted in a traditional open surgical approach.

Percutaneous placement of the apparatus 10 starts by accessing a bodily vessel with a delivery device (not shown) capable of delivering the apparatus. For instance, a guide wire (not shown) may be introduced into the vasculature via a vascular or intercostal opening. In the case of a vascular opening, vascular access may be through a peripheral venous access site. For example, the superior vena cava may be accessed through a variety of peripheral access sites, such as the internal jugular vein, while the inferior vena cava may be accessed through the femoral vein. Alternatively, percutaneous penetration can be achieved within the intercostal spaces of a patient's rib cage as known in the art, whereby the tricuspid valve 48 is then accessed surgically through the right atrium.

Once percutaneous access is achieved, the delivery device is advanced to the heart intravascularly and positioned adjacent the tricuspid valve 48. Depending on the point of vascular access, the approach to the tricuspid valve 48 may be antegrade and require entry into the right atrium via the superior vena cava. Alternatively, the approach to the tricuspid valve 48 may be retrograde and require entry into the right atrium via the inferior vena cava.

Figure 4:
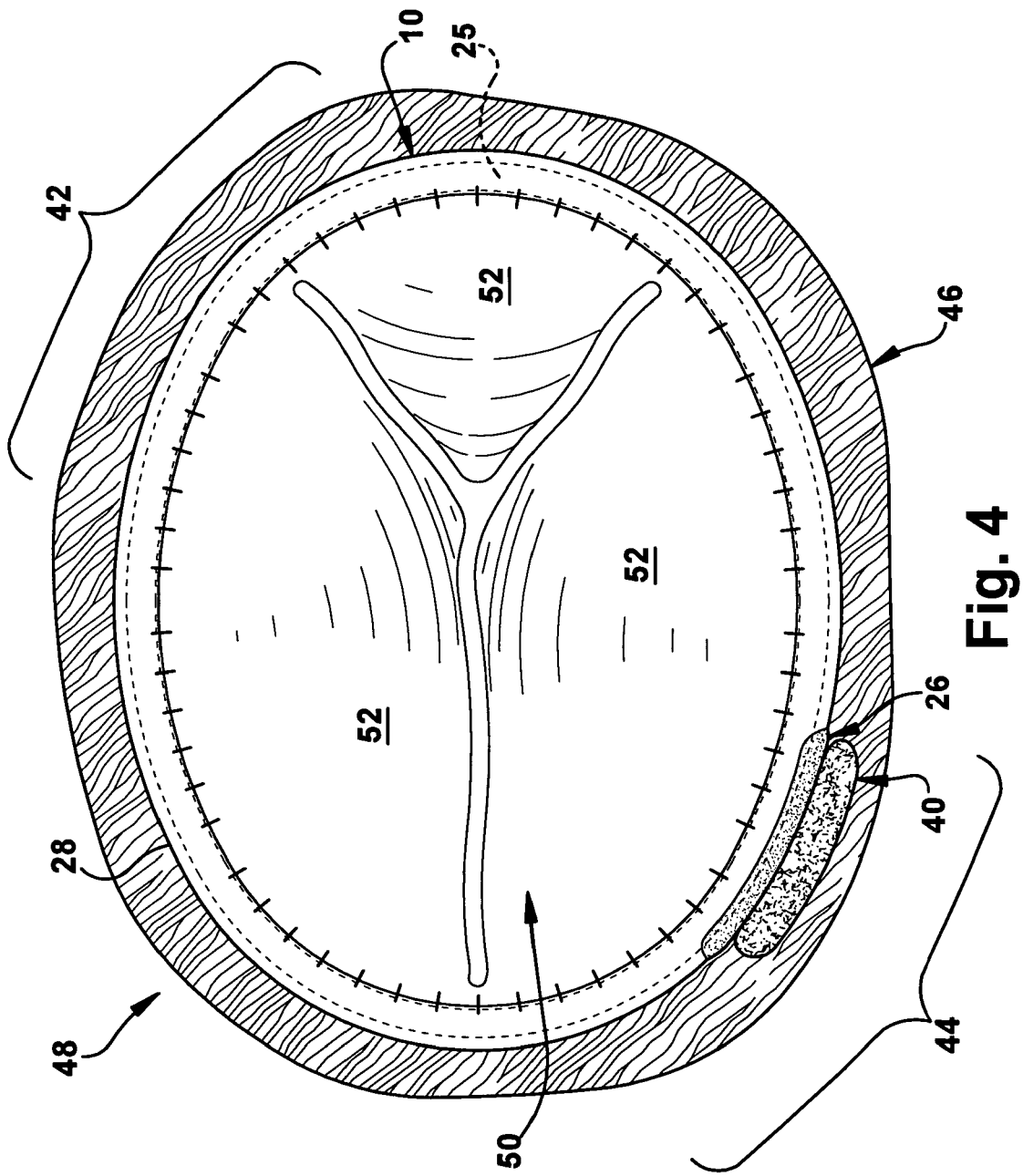
FIG. 4 is a perspective view of the apparatus implanted within the annulus of a tricuspid valve.

Proper orientation of the apparatus 10 is necessary for correctly positioning the apparatus within the tricuspid valve 48. The orientation of the apparatus 10 in relation to cardiac structures is of concern. In particular, cardiac structures to which orientation is desired include the 3D shape of the tricuspid valve annulus 46 and the AV node 40. Studies show that the tricuspid valve 48 has a non-planar annulus 46. Successful valve replacement procedures, therefore, depend upon the ability of a replacement valve to correctly conform to the anatomical shape of the tricuspid valve annulus 46. The apparatus 10 of the present invention has a 3D shape which allows the apparatus to conform entirely to the shape of the tricuspid valve annulus 46 when implanted as shown in FIG. 4. Proper orientation may be achieved by a variety of means including, for example, tactile feedback, visualization (e.g., enhanced echogenic and/or fluoroscopic visibility), and blood flow patterns.

After placing the apparatus 10 within the tricuspid valve annulus 46, the apparatus is positioned such that the anterior and posterior portions 16 and 14 are respectively positioned against the anterior and posterior aspects 44 and 42 of the tricuspid valve annulus. The apparatus 10 is positioned proximate to the valve annulus 46 and attached to surrounding tissue in a plurality of accepted manners, including, for example, suturing, stapling, pinning, clipping, or any other biologically-compatible attachment technique. When the apparatus 10 is sufficiently attached, the delivery device is then removed. With the apparatus 10 implanted, the tricuspid valve 48 is rendered competent while the normal function of the AV node 40 is preserved.

In a normal heart rhythm, the sinoatrial node (not shown) generates an electrical impulse that travels through the right atrium and left atrial muscles (not shown) producing electrical changes. The electrical impulse then continues to travel through the specialized tissue of the AV node 40, which conducts electricity at a slower pace. Excessive pressure on the AV node 40 can disrupt the normal function of the AV node. The cushioning means 30 of the present invention serves to mitigate the force or shock of the apparatus 10 against the AV node 40. The normal physiological function of the AV node 40 is not perturbed when the apparatus 10 is positioned within the tricuspid valve annulus 46 as the cushioning means 30 imparts the cushioned section 26 with the ability to flex and conform to the AV node.

From the above description of the invention, those skilled in the art will perceive improvements, changes and modifications. Such improvements, changes and modifications within the skill of the art are intended to be covered by the appended claims.

Having described the invention, I claim:

1. An apparatus for implantation in the annulus of a tricuspid valve, the annulus having an anterior annulus aspect, a posterior annulus aspect, and an atrioventricular (AV) node located adjacent the anterior annulus aspect, the apparatus comprising:

an ovoid main body portion having an inner layer and an outer layer, the inner layer being an expandable support member and the outer layer being a biocompatible covering;

the main body portion including an anterior body segment adapted for placement adjacent the anterior annulus aspect of the tricuspid valve, a posterior body segment located opposite the anterior body portion and adapted for placement adjacent the posterior annulus aspect of the tricuspid valve, and oppositely disposed left and right side body segments extending between the anterior and posterior body segments;

at least two valve leaflets secured within the main body portion and coaptable to permit unidirectional flow of blood; and a cushioned section attached to the outer layer of the main body portion, the cushioned section having a first thickness and the main body portion having a second thickness which is less than the first thickness, the cushioned section coextending with only a portion of the main body portion and adapted for placement adjacent the AV node, the AV node being located adjacent the anterior aspect of the annulus of the tricuspid valve.

2. The apparatus of claim 1, wherein the main body portion has a three-dimensional shape which conforms to a three-dimensional shape of the annulus of the tricuspid valve.

3. The apparatus of claim 1, wherein the outer layer is adapted for attachment to the annulus of the tricuspid valve.

4. The apparatus of claim 1, wherein the cushioned section is integrally formed with the main body portion.

5. A method for implanting an apparatus in the annulus of a tricuspid valve, the annulus having an anterior annulus aspect, a posterior annulus aspect, and an atrioventricular (AV) node located adjacent the anterior annulus aspect, the method comprising the steps of:

providing an apparatus having an ovoid main body portion, an inner layer comprising an expandable support member, and an outer later comprising an biocompatible covering;

the apparatus further having at least two valve leaflets secured within the main body portion and coaptable to permit unidirectional flow of blood, and a cushioned section attached to the outer layer of the main body portion and having a first thickness, the main body portion having a second thickness which is less than the first thickness, the cushioned section coextending with only a portion of the main body portion;

the main body portion having an anterior body segment, a posterior body segment located opposite the anterior body portion, and oppositely disposed left and right side body segments extending between the anterior and posterior body segments;

placing the apparatus within the annulus of the tricuspid valve;

positioning the anterior body segment adjacent the anterior annulus aspect;

positioning the posterior body segment adjacent the posterior annulus aspect;

positioning the cushioned section adjacent the AV node; and securing the apparatus, as positioned, within the annulus of the tricuspid valve.

6. The method of claim 5, wherein the main body portion has a three-dimensional shape which conforms to a three-dimensional shape of the annulus of the tricuspid valve.

7. The method of claim 5 wherein the step of securing the apparatus, as positioned, within the annulus of the tricuspid valve includes the step of attaching the outer layer to the annulus of the tricuspid valve.

* * * * *